(12) United States Patent
Ashman

(10) Patent No.: US 6,471,703 B1
(45) Date of Patent: Oct. 29, 2002

(54) VARIABLE ANGLE CONNECTION ASSEMBLY FOR A SPINAL IMPLANT SYSTEM

(75) Inventor: Richard B. Ashman, New Orleans, LA (US)

(73) Assignee: SDGI Holdings, Inc., Wilmington, DE (US)

( * ) Notice: Subject to any disclaimer, the term of this patent is extended or adjusted under 35 U.S.C. 154(b) by 198 days.

(21) Appl. No.: 09/710,750

(22) Filed: Nov. 9, 2000

Related U.S. Application Data

(63) Continuation-in-part of application No. 09/536,530, filed on Mar. 28, 2000, which is a continuation-in-part of application No. 09/296,104, filed on Apr. 21, 1999, now Pat. No. 6,183,473.

(51) Int. Cl.[7] ................................................ A61B 17/70
(52) U.S. Cl. .......................................... 606/61; 606/73
(58) Field of Search ............................. 606/61, 73, 72, 606/62, 60, 63, 64, 65, 86, 54, 87, 59; 623/17.11, 17.15, 17.16; 411/388, 389, 396, 397

(56) References Cited

U.S. PATENT DOCUMENTS

| | | |
|---|---|---|
| 5,047,029 A | 9/1991 | Aebi et al. |
| 5,053,034 A | 10/1991 | Olerud |
| 5,129,900 A | 7/1992 | Asher et al. |
| 5,254,118 A * | 10/1993 | Mirkovic ..................... 606/60 |
| 5,261,909 A | 11/1993 | Sutterlin et al. |
| 5,282,801 A | 2/1994 | Sherman |
| 5,425,732 A | 6/1995 | Ulrich |
| 5,487,744 A | 1/1996 | Howland |
| 5,527,314 A | 6/1996 | Brumfield et al. |
| 5,549,607 A * | 8/1996 | Olson et al. ................... 606/61 |
| 5,562,661 A | 10/1996 | Yoshimi et al. |
| 5,562,662 A * | 10/1996 | Brumfield et al. ............ 606/61 |
| 5,584,831 A | 12/1996 | McKay |
| 5,611,800 A | 3/1997 | Davis et al. |
| 5,634,925 A * | 6/1997 | Urbanski ..................... 606/61 |
| 5,643,262 A * | 7/1997 | Metz-Stavenhagen et al. ........................... 606/60 |
| 5,643,263 A | 7/1997 | Simonson |
| 5,741,255 A * | 4/1998 | Krag et al. ................... 606/61 |
| 5,947,967 A | 9/1999 | Barker |
| 5,976,135 A * | 11/1999 | Sherman et al. .............. 606/61 |
| 5,980,521 A | 11/1999 | Montague et al. ............ 606/61 |
| 6,001,098 A * | 12/1999 | Metz-Stavenhagen et al. ........................... 606/60 |
| 6,030,388 A | 2/2000 | Yoshimi et al. |
| 6,050,997 A | 4/2000 | Mullane |
| 6,187,005 B1 * | 2/2001 | Brace et al. .................. 606/61 |
| 6,309,390 B1 * | 10/2001 | Le Couedic et al. .......... 606/61 |
| 6,328,739 B1 * | 12/2001 | Liu et al. ..................... 606/61 |

* cited by examiner

*Primary Examiner*—Amy B. Vanatta
(74) *Attorney, Agent, or Firm*—Woodard, Emhardt, Naughton Moriarty & McNett

(57) ABSTRACT

A spinal implant assembly comprises a connection assembly, an elongated spinal implant, and a bone fastener, such as a bone screw, engaged within a vertebra. The connection assembly includes a body defining a first opening for receiving the elongated spinal implant, a second opening for receiving a bone fastener and a plug. The first opening is perpendicular to and overlapping the second opening to allow direct contact between the spinal implant and the bone fastener. The second opening includes a plug slot having a wall at an end opposite the first opening that defines an engagement surface. The plug includes a mating surface that forms an interlocking engagement with the engagement surface of the wall. An opposite second surface of the plug defines a groove for receiving the elongated stem of the bone fastener adjustable to a desired angular orientation and height. The body can include a first and a second side walls converging toward the center of the second opening with a gap to receive the stem of the bone fastener. The connection assembly further comprises means for urging the elongated spinal implant to press against the bone fastener and the plug which, subsequently, is pressed against the engagement surface of the wall.

20 Claims, 9 Drawing Sheets

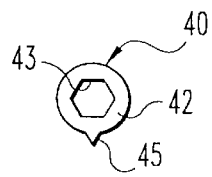
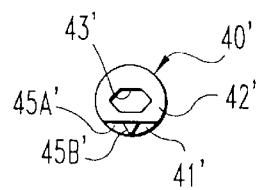
Fig. 5        Fig. 7
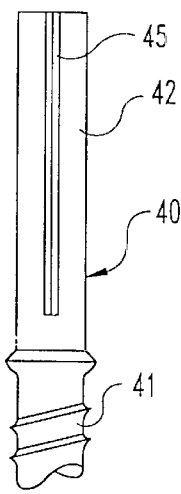
Fig. 6
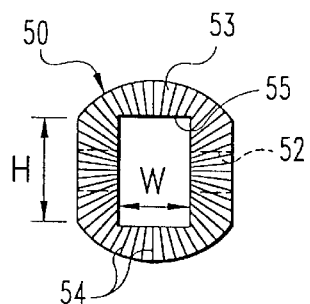
Fig. 8
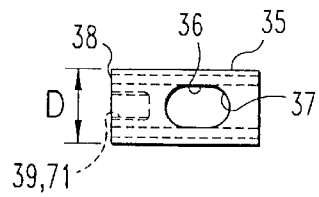
Fig. 9
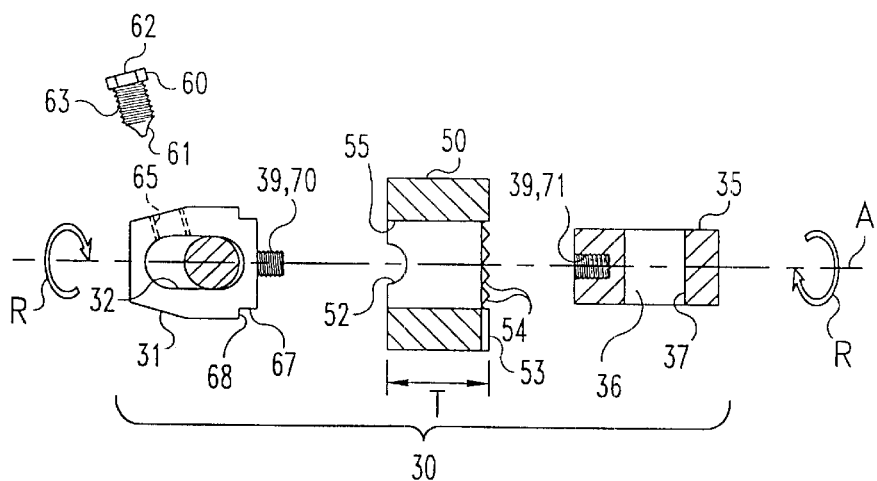
Fig. 10

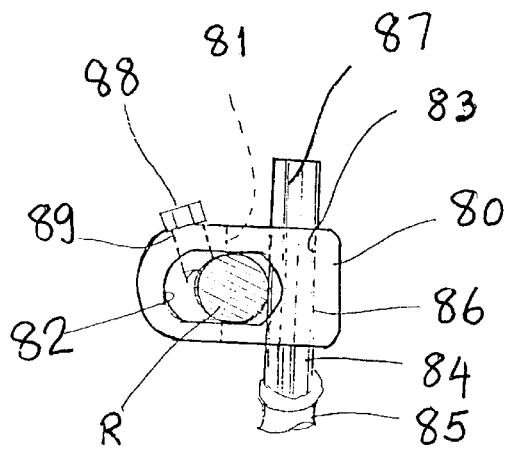
FIG. 11
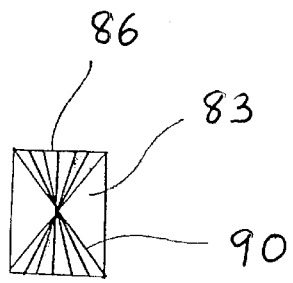
FIG. 12
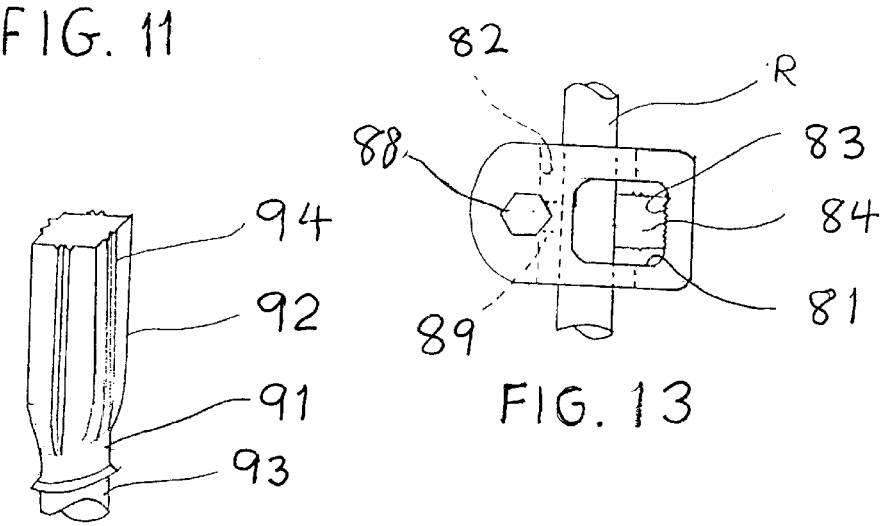
FIG. 14
FIG. 13

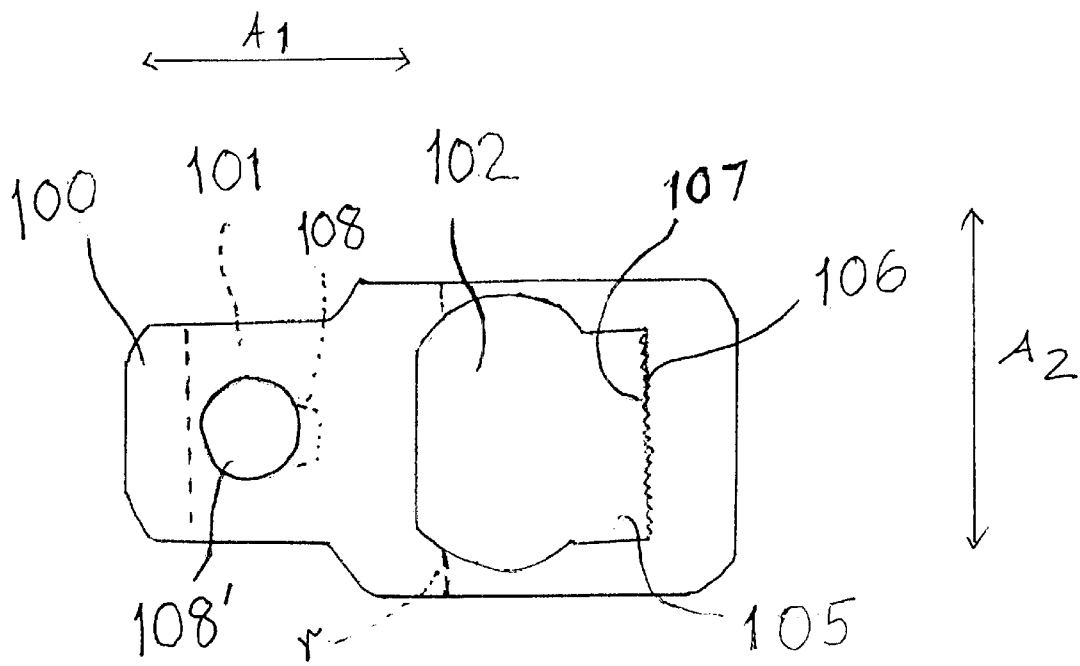
FIG 17
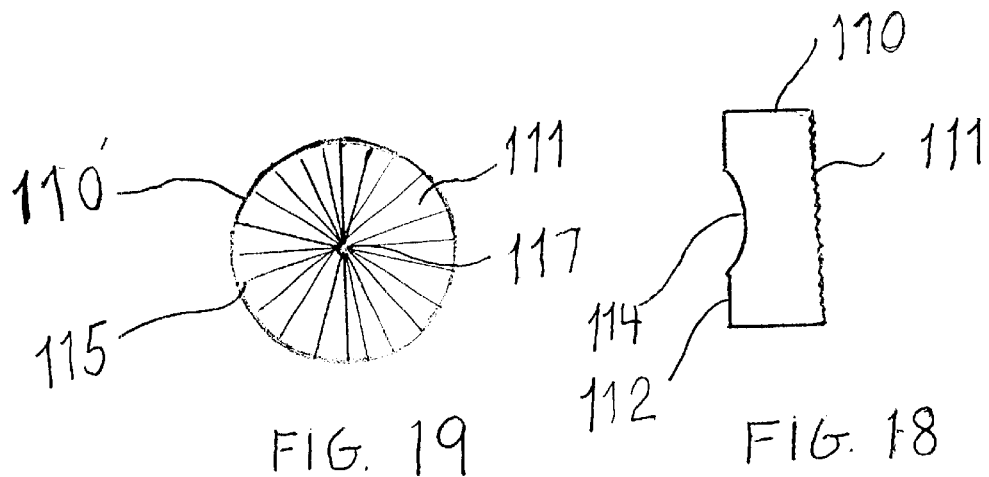
FIG. 19
FIG. 18

VARIABLE ANGLE CONNECTION ASSEMBLY FOR A SPINAL IMPLANT SYSTEM

CROSS-REFERENCE TO RELATED U.S. PATENT APPLICATION

This is a continuation-in-part application of a co-pending U.S. patent application Ser. No. 09/296,104, filed Apr. 21, 1999 now U.S. pat. No. 6,183,473. And a continuation-in-part application Ser. No. 09/536,530, filed Mar. 28, 2000.

BACKGROUND OF THE INVENTION

The present invention relates generally to the field of spinal implant systems, and particularly systems that employ elongated spinal implants, such as a rod and plates, connected at various locations along the spinal column. More particularly, the invention concerns a connection assembly that provides variable angle and variable height adjustability to the elongated spinal implant relative to a bone fastener engaged to the spine.

Several spinal fixation systems have been developed for use in correcting and stabilizing sections of the spinal column and facilitating spinal fusion. In one such system, a bendable elongated spinal implant, such as a rod, is longitudinally disposed adjacent the vertebral column and then secured to various vertebrae along the length of the column by way of a number of bone fasteners or fixation elements. A variety of bone fasteners can be utilized, such as hooks or bone screws, which are configured to engage specific portions of a vertebra.

An example of one such system is the TSRH® Spinal System of Sofamor Danek Group, Inc. In this system, various hooks and bone screws are engaged to a spinal rod by way of eyebolts. In early versions of the TSRH® Spinal System, the vertebral hooks and bone screws were attached to the spinal rod at a fixed orientation, usually projecting perpendicularly below the rod. At the time, the TSRH® Spinal System presented a significant advance over prior systems in its versatility, strength of fixation, and ease of implantation.

However, one drawback faced by the original TSRH® Spinal System, as well as the other prevalent fixation systems, was that a surgeon was required to make significant adjustments to the contour of the bendable rod so that the bone fasteners could solidly engage the vertebral bodies. What was needed, then, was a bone fastener that could be connected to the spinal rod at a variable angle. In order to address this need, the TSRH® Variable Angle Screw was developed, as described in U.S. Pat. No. 5,261,909. This Variable Angle Screw utilized the same TSRH® eyebolt to achieve a connection to a spinal rod. In addition, the Variable Angle system incorporated a washer that fit over the eyebolt, engaged the spinal rod within a groove in one surface of the washer, and provided a radially splined surface facing the bone fastener. The bone fastener had a complementary splined surface so that the fastener could be situated at variable angular orientations relative to the spinal rod. A nut threaded onto the post of the eyebolt clamped all the components together to complete the assembly.

The Variable Angle Screw system of the '909 Patent presented a significant advance over prior rod-based implant systems. The system of the '909 Patent was relatively compact and required a minimal number of parts yet was able to accomplish a solid fixation of the bone fastener to the rod at a wide range of angular orientations. One drawback of the system was that the eyebolt-nut combination required side-tightening of the nut to clamp the system together. This side-tightening aspect required a larger surgical site about the spine so that a wrench could be manipulated. To address this difficulty, a top-tightening assembly was developed as disclosed in U.S. Pat. No. 5,282,801. The clamp assembly depicted in the '801 Patent replaced the eyebolt and nut with a clamp body having a T-bar against which the head of the variable angle bone fastener was clamped. In addition, while the original TSRH® System relied upon tightening a nut against the variable angle bone screw, the top-tightening approach of the '801 Patent utilized a set screw that acted against the spinal rod to push the spinal rod into the interlocking washer, and ultimately against a complementary spline face of the variable angle screw. With this system, the variable angle capability was retained, while a top-tightening feature was added.

With the addition of the top-tightening capability, the more recent TSRH® Spinal System has provided surgeons with a great deal of flexibility in the placement and orientation of bone fasteners, such as hooks and screws, relative to a spinal rod. The Variable Angle components greatly reduce the need to manipulate and bend the spinal rod to conform to the patient's anatomy. Even with the great improvements presented by the TSRH® Spinal System, a certain amount of shaping or contouring of the spinal rod has still been required. Specifically, the rod must be shaped so that at the point of attachment of the bone fastener, the rod is the same distance from the vertebral body as the splined or interdigitating portion of the bone fastener. This vertical or height alignment is necessary so that the variable angle components are properly aligned for accurate connection when the assembly is clamped together. Thus, the spinal surgeon still has to spend a certain amount of time shaping the spinal rods during the surgery so that the fixation system can be properly implanted.

In order to address this difficulty, later systems were developed that provided for a certain degree of vertical adjustability. By vertical or height adjustability, it is meant adjustment along the length of the bone fastener. Adjustment in this dimension allows the rod to be situated at varying distances from the spine, or oriented with a pre-set contour regardless of the location of the fastener.

An adaptation of the original variable angle screw concept of the '909 Patent is presented in U.S. Pat. No. 5,611,800. This system retained the yoke configuration of the bone screw in the '909 Patent, but added a multifaceted connecting feature on both surfaces of the yoke. While the '800 Patent system added height adjustability, it did so at the cost of a more complicated connector structure with four specially machined interdigitating surfaces.

Another approach has been suggested in U.S. Pat. No. 5,643,263. The connection assembly in the '263 Patent uses a Schanz-type bone screw rather than the yoke bone screw of the '909 Patent.

Thus, the screw described in the '263 Patent includes an elongated smooth shank portion. The connection assembly also adds a second washer disposed between the original washer and the smooth shank of the bone screw. The interdigitating feature exists between the contacting faces of the adjacent washers. The variable height is accomplished by a groove provided in the opposite surface of the additional washer that allows the connection assembly to slide along the shank of the bone screw until it is finally clamped together by a set screw.

While the connection assembly shown in the '263 Patent goes a step further toward an easy-to-implant variable angle, variable height assembly, it too has left some room for improvement. For example, the connector assembly of the '263 Patent requires an additional washer that adds to the number of components that must be manipulated by the surgeon. In addition, the added washer increases the lateral profile of the implant assembly. In certain regions of the spine, such, as the thoracic and cervical regions, there is limited space transverse to the vertebral bodies. An optimal spinal implant system that has universal applicability should have as small a lateral profile as possible.

Yet another approach for achieving variable angular orientation of the spinal implant assembly has been suggested in U.S. Pat. No. 5,947,967. The connection assembly shown in '967 includes a body defining a tapered outer surface and an internal tapered washer fitting over the tapered outer surface of the body. The washer includes a slot to receive the bone screw which can lock the screw in position by frictional engagement with the tapered outer surface of the body. Although the connection assembly in '967 allows the bone screw to adopt variable angular orientations relative to the rod, it does not provide easy access for readjustibility once the connection assembly is fixed to a particular position.

A need has remained for a spinal implant system that not only provides a reliable connection between a bone fastener and an elongated spinal implant or a rod that spans along the spine, while permitting variable angular and height between the two components, but also provides an easy access for reorientation and readjustment of the components. A need has also remained for a spinal implant system that has reduced bulk or prominence to avoid other spinal features and to be undetectable along the patient's back.

SUMMARY OF THE INVENTION

In order to address the unresolved detriments of prior implant systems, the present invention contemplates a variable angle/variable height connection assembly for a spinal implant system. In one embodiment of the invention, a connection assembly includes a first member or body that defines an opening through which an elongated spinal implant, such as a spinal rod, can extend. A second member is provided that includes a second opening through which extends an elongated stem or shank of a bone fastener, such as a bone screw or hook. In some embodiments, the two members are attached by a connecting means that allows the members to pivot relative to each other about a connection axis. This connecting means thus provides a mechanism for variable angular orientations of the bone fastener relative to the elongated spinal implant. The second opening in the second member adds the height adjustment capability.

In another aspect of the invention, the two openings are substantially perpendicular and overlapping. The bone fastener opening has a width that affords variable angular orientations of the bone fastener. In certain embodiments, a wall of the bone fastener opening opposite the spinal implant opening can define an engaging surface. The stem of the bone fastener can be cylindrical or can have substantially flat surfaces configured with projecting ribs for interlocking with the engaging surface. A set screw can be used as a means to urge the spinal implant to press against the bone fastener and the bone fastener against the engaging surface.

In another embodiment of the invention, a connection assembly includes a body defining a first opening sized to receive the elongated spinal implant therethrough and a second opening sized to allow variable angular placement of the bone fastener therethrough. The first opening is elongated along a first axis, and the second opening is elongated along a second axis substantially perpendicular to the first axis. The second opening overlaps the first opening to allow direct contact between the elongated spinal implant and the elongated stem of the bone fastener therein. The second opening is configured to include a plug slot. The plug slot includes a wall opposite the first opening, and the wall defines an engaging surface thereon. The body further includes a first bore intersecting the first opening at an opposite end of the wall.

The connection assembly further includes a plug that can fit snugly within the plug slot. The plug has a mating surface matable to the engagement surface of the wall, and a second surface defining a groove for contacting the elongated stem of the bone fastener. The engagement surface of the wall preferably includes a plurality of radiating splines and the mating surface of the plug includes a plurality of complementary radiating splines. Alternatively, the engagement surface of the wall can include a raised pattern or knurling, and the mating surface of the plug includes a complementary raised pattern or knurling.

Further, the connection assembly can include means extending through the first bore for urging the elongated spinal implant against the elongated stem of the bone fastener and simultaneously urging the elongated stem of the bone fastener against the engagement surface of the wall. When the urging means is loosened, the plug can be rotated so that the groove can receive the elongated stem of the bone fastener at a desired height and angular orientation. Since the plug is accessible from the top side of the connection assembly, it is easy for the surgeon to manipulate or reposition the connection assembly by simply rotating the plug. When the urging means is tightened, the connection plug is pressed against the wall and the spinal assembly is fixed to in final position on the spine.

In an alternative embodiment, a connection assembly includes a body having all the features in the previous embodiment described immediately above. In addition, the body further defines a second bore intersecting the second opening at the center of the wall for receiving a securing means for fastening the plug to the plug slot. In this embodiment, the plug further defines a center bore alignable to the second bore of the body when it is inserted in the plug slot. This embodiment of the connection assembly also includes a securing means defining a securing member extendable through the second bore of the body and the center bore of the plug in the plug slot. The securing member can be a second set screw or a rivet, while both the second bore and the center bore can be threaded to receive the second set screw. The securing member can optionally be loosened or tightened after the assembly is fixed in a particular position on the spine. When the securing member is loosened, the plug can be rotated for angular adjustment for receiving the elongated stem of the bone fastener. When the securing member is tightened, the plug is secured against the engagement wall of the body. In this way, the angular orientation of the spinal implant assembly can be adjusted or readjusted without having to disturb the whole spinal implant system.

In this alternative embodiment, the connection assembly also includes means for urging the elongated spinal implant against the elongated stem of the bone fastener. The urging means includes an urging member extendable through the first bore to contact a spinal implant. The urging member can be a set screw, and the first bore is threaded to receive the set screw. The set screw includes an engagement tip for contacting the spinal implant within the first opening. The set screw can be threaded into the first bore, and as the set screw is driven further into first bore, the engagement tip urges the spinal rod toward the stem of the bone fastener. Continued tightening the set screw increases the clamping force between the spinal implant, the stem of the bone fastener and the plug that has been secured against the engagement wall of the body. Optionally, the securing member only secures the plug inside the plug slot while the plug is rotatable about the center bore axis. Only when the urging member is tightened, the clamping force between the spinal implant, the stem of the bone fastener and the plug presses the mating surface of the plug against the engagement surface of the wall.

In another feature of the present invention, the second opening includes a first side wall and a second side wall, the side walls are raised and converging toward each other leaving a gap sufficient to receive the bone fastener therethrough. Thus, in this feature, the gap essentially acts as a fulcrum about which the body can be pivoted relative to the elongated stem of the fastener to properly orient the connection assembly.

In yet another feature of this invention, a spinal implant assembly, includes a connection assembly as described above, and a bone fastener having an end being an elongated stem and an opposite end being a screw or a hook. The elongated stem in a preferred embodiment is cylindrical and smooth, and sized to fit the groove on the second surface of the plug.

It is one object of the present invention to provide a spinal implant system for variable angle/variable height adjustment. Another objective is to provide spinal implant system components that can be easily clamped together with reduced bulk or prominence to avoid anatomical features and to insure a solid fixation of the instrumented portion of the spine.

Significant benefits are achieved by features of the invention that permit angular adjustment of the spinal implant assembly while most components have been fixed in place. These and other objects and benefits of the invention will be made clear upon consideration of the following written description and accompanying figures.

DESCRIPTION OF THE FIGURES

FIG. 5 is a top elevational view of a bone engaging fastener used with the connection assembly shown in FIGS. 3–4.

FIG. 6 is a side elevational view of the bone fastener shown in FIG. 5.

FIG. 7 is a top elevational view of an alternative embodiment of a bone fastener for use with the connection assembly shown in FIGS. 3–4.

FIG. 8 is an end elevational view of an interface washer component of the connection assembly as shown in FIGS. 3–4.

FIG. 9 is a top elevational view of a second member of the connection assembly shown in FIGS. 3–4.

FIG. 10 is an exploded, partial cross section view, of the components of the connection assembly shown as FIGS. 3–4.

FIG. 11 is a side elevational view of a connection assembly in accordance with still a further embodiment of the invention.

FIG. 12 is an end elevational view of a surface of a wall of a bone fastener opening on the connection assembly shown in FIG. 11.

FIG. 13 is an end elevational view of the connection assembly shown in FIG. 11.

FIG. 14 is a side perspective view of an alternative bone fastener.

FIG. 17 is a top elevational view of a body of a connection assembly in accordance with the preferred embodiment as shown in FIG. 15.

FIG. 18 is a top elevational view of a plug in accordance with an embodiment of the invention.

FIG. 19 is a side elevational view showing a first surface of the plug as shown in FIG. 18.

DESCRIPTION OF THE PREFERRED EMBODIMENTS

Figure 1:
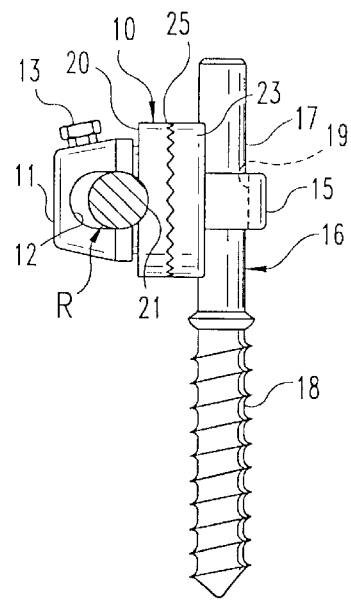
FIG. 1 is a side elevational view of a spinal implant connection assembly according to the prior system disclosed in U.S. Pat. No. 5,643,263.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention contemplates a variable angle and variable height connection assembly for connecting a bone fastener, such as a bone screw or hook, to an elongated spinal implant, such as a spinal rod, bar or plate. It is understood that the components of this connection assembly are formed of a medical grade material, preferably a metal such as stainless steel or titanium. It is also understood that the components are sized for introduction and implantation within the spine of a human patient. It is contemplated that the invention can be implanted at all levels of the spine, namely the cervical, thoracic, and lumbar levels, and from the posterior or anterior aspects of the spine. The components can be sized appropriately for each of the levels of the spine, with the overall size of the components being determinable by the ordinarily skilled artisan in the field of spinal implants.

Although the present invention has broad applicability, it is best understood with comparison to a prior art spinal implant connection assembly described in U.S. Pat. No. 5,643,263. In particular, the connection assembly 10 shown in FIG. 1 includes a rod connection member 11 that defines an elongated opening 12 through which a spinal rod R extends. A set screw 13 is threaded through the rod connection member 11, into the opening 12 and in contact with the spinal rod R.

Figure 2:
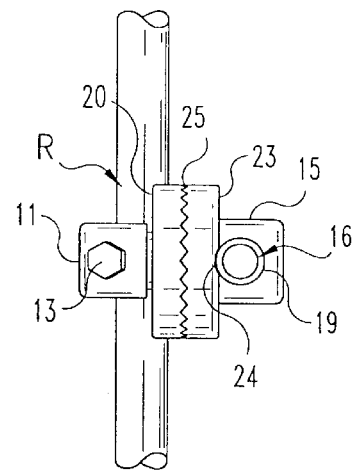
FIG. 2 is a top elevational view of the spinal implant assembly as shown in FIG. 1.

This prior art connection assembly 10 further includes a bolt connection member 15 defining a bolt opening 19 through which a bolt 16 extends. The bolt includes a non-threaded, smooth cylindrical post at one end and bone engaging threads 18 at an opposite end. The bolt connection member 15 is rotatably connected to the rod connection member 11 in a manner described in the '263 Patent with reference to FIGS. 1 and 2 of that patent, which description is incorporated herein by reference. Thus, the bolt connection member 15 is free to pivot or rotate relative to the rod connection member 11, which means that the bolt 16 can assume variable angular orientations relative to the rod R.

Figure 3:
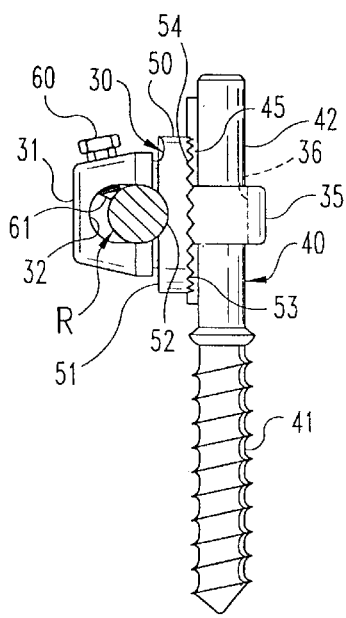
FIG. 3 is a side elevational view of a variable angle connection assembly according to one embodiment of the present invention.
Figure 4:
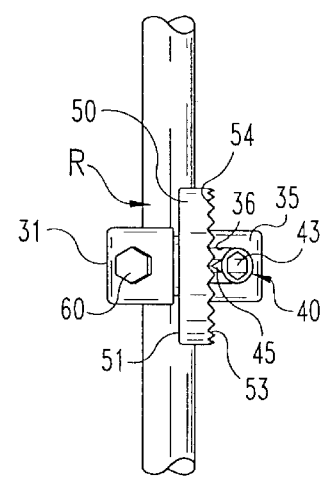
FIG. 4 is a top elevational view of the connection assembly as shown in FIG. 1.

In order to fix this angular relationship, the connection assembly 10 includes a rod interface washer 20 and a bolt interface washer 23. The rod interface washer 20 includes an engagement groove 21, which receives the spinal rod R. Likewise the bolt interface washer 23 includes an engagement groove 24 into which is disposed the post 17 of the bolt 16. A spline interface 25 is provided between the two interface washers 20 and 23. Turning now to FIGS. 3–4, a connection assembly 30 is provided that permits similar variable angle and variable height adjustments to the position of the bone fastener relative to an elongated spinal implant. The elongated spinal implant can take a variety of forms, such as a rod or a plate. As a rod, the spinal implant can have a circular or a non-circular cross-section that is preferably configured to permit attachment of a connection assembly 30 at various positions along the length of the implant. Preferably, although not essentially, the spinal implant can also be configured to permit rotation of the connection assembly about the longitudinal axis of the implant.

In accordance with the preferred embodiment on the invention, the connection assembly 30 includes a first member 31 that defines a transverse opening 32 therethrough. The opening 32 is slightly elongated and is sized to receive an elongated spinal implant therethrough. More particularly the opening 32 is sized to slidingly receive a spinal rod R. The connection assembly 30 also includes a second member 35 that defines a second opening 36 therethrough. The opening 36 is sized to slidingly receive the stem of a bone fastener therethrough. The opening 36 is also elongated in a direction toward the first member 31.

As shown best in the detail view of FIG. 9 and the exploded view of FIG. 10, the connection assembly 30 includes connecting means 39 between the first member 31 and the second member 35. This connecting means 39 is configured to permit relative pivoting between the two members about a connection axis A. More particularly, the two members can be individually rotated in the direction of the arrows R as shown in FIG. 10. The connecting means 39 can take a variety of forms. For instance, the connecting means 39 can constitute the snap-together swivel connection shown in FIGS. 1 and 2 of U.S. Pat. No. 5,643,263, and described at column 2, lines 31–46 of the patent which disclosure is incorporated here and by reference.

In the most preferred embodiment, the connecting means 39 includes a threaded post 70 extending from an end portion 67 of the first member 31. The connecting means 39 also includes a mating threaded bore 71 defined in the end face 38 of the second member 35. The relative rotation between the two members 31 and 35 can be achieved by threading or unthreading the post 70 relative to the bore 71. The pitch of the threads of the components means 39 can be controlled so that the separation between the first member 31 and second member 35 does not vary significantly even as the relative angular position between the two components changes. In addition, the threads on either or both of the post 70 and bore 71 can be configured in the nature of locking threads so the two components will maintain their angular positions prior to final clamping. As a further alternative, the length of the threads on either the post 70 or bore 71 can be limited since it is anticipated that only limited angular variations would be necessary in the use of the connection assembly 30. It is generally anticipated that angular variations of ±20–25° from the vertical would satisfy most spinal anatomies.

Referring back to FIGS. 3 and 4, as well as FIGS. 5 and 6, the bone fastener 40 includes a bone engaging portion 41 that is configured for attachment to a portion of the spine. In the illustrated embodiment, the bone engaging portion 41 constitutes bone engaging threads in the nature of a pedicle screw. As indicated above, other bone attachment configurations are contemplated by the invention.

The fastener 40 also includes an elongated stem 42 at the top portion of the fastener. An internal hex 43 (see FIGS. 4 and 5) is provided for engaging a tool for screwing the bone fastener 40 into a vertebra. Alternatively, an external hex or driving portion can be provided for engagement by an appropriate driving tool. Where the bone fastener 40 is a spinal hook, the internal hex 43 is not essential, but gripping recesses may be added to the stem.

In one aspect of the present invention, the bone fastener 40 includes an interface element 45 that is configured for interlocking engagement with the interface washer 50. Details of the interface washer 50 are shown in FIGS. 3, 4, and 8. The washer 50 includes a first face 51 that is orientated to the elongated spinal implant, or rod R. A rod groove 52 is formed in the first face 51. The rod groove is defined at a radius that is smaller than the radius of the spinal rod R. This design for the rod groove 52 is in accordance with the "3-point-shear clamp" feature of the TSRH® system. While the preferred embodiment of the present invention contemplates the use of a rod groove 52 for a circular rod R, other clamping or attachment mechanisms are contemplated. For example, the spinal rod R can be formed of a relatively softer material than the interface washer 50, while the first face 51 of the washer can include surface features configured to penetrate the rod R. Other rod clamping arrangements can be contemplated that can solidly fix the interface washer 50 to the rod R to prevent relative movement under spinal loads.

The interface washer 50 includes an opposite second face 53, shown most clearly in FIG. 8. This second face incorporates an interface element 54 that cooperates with the interface element 45 of the bone fastener 40. In accordance with one embodiment of the invention, the interface element 54 of the washer 50 includes a plurality of radially arranged splines. This spline configuration can be similar to the splined washer disclosed in U.S. Pat. No. 5,261,909, which can alternatively be described as alternating ridges or teeth. The radial pattern of the splines converges at the rotational center of the washer 50, or more particularly about the opening 55.

The interface element 45 of the bone fastener 40 in this embodiment constitutes a rib that is configured to reside between the splines of the interface element 54 on the second face 53 of the washer 50. The rib or interface element 45 of the bone fastener 40 preferably extends along substantially the entire length of the elongated stem 42. In this way, the height position of the stem 42 can be varied relative to the interface washer 50, while still retaining the interlocking relationship between the splines and the rib.

In one embodiment of the bone fastener 40, the spline or interface element 45 projects from the outer diameter of the stem 42 as shown in FIG. 5. In an alternative embodiment, shown in FIG. 7, a bone fastener 40' includes a stem 42' that defines a truncated face 45A'. The interface element can then constitute a rib 45B' projecting from the truncated face. The bone fastener 40' can then be identical in all other aspects to the bone fastener 40 shown in FIGS. 5–6. The alternative bone fastener 40' shown in FIG. 7 requires different machining to fabricate than the bone fastener 40 shown in FIG. 5. One advantage of the alternative fastener 40' is that the truncated face 45A' shortens the lateral profile since the elongated stem 42' of the fastener 40' can be situated closer to the spinal rod R when the connection assembly is clamped together.

To ensure fixation at variable angular positions, the washer 50 must remain stationary relative to the second member 35 and bone fastener 40. Referring to FIG. 8, the interface washer 50, includes an opening 55 that has a width W and a height H. Preferably the opening 55 is non-circular and conforms to the outer profile of the end portion 67 of the first member 31. With this configuration, the washer 50 can be slid onto the end portion 67 until it contacts a shoulder 68. The complementary non-circular profiles of the end portion 67 and opening 55 prevent rotation of the washer 50 relative to the first member 31. In this way, the washer can act as a rotational anchor for the bone fastener 40 when the connection assembly 30 is clamped together.

In order for the second member 35 to be permitted to rotate relative to the first member 31, the second member 35 is preferably cylindrical. The second member 35 can then have a diameter D that is less than the width W of the opening 55 in the interface washer 50. With this arrangement, the second member 35 can rotate relative to the first member even when the washer 50 is disposed about the first member and second member.

Returning again to FIGS. 3, 4, 9, and 10, the connection assembly 30 also includes means for urging the elongated implant, or rod R, and the elongated stem 42 of the bone fastener 40 together. In a preferred embodiment, this means for urging includes a set screw 60 having an engagement tip 61 that is configured to contact the spinal rod R. The tip 61 can have a variety of shapes for translating the longitudinal motion of the set screw to a lateral force on the rod. The screw also includes a head 62 for engagement by a driving tool, and a series of screw threads 63 that are configured to be threaded into a complementary threaded bore 65.

The bore 65 is defined in the first member 31 and intersects the opening 32. The arrangement and alignment of the threaded bore 65 and set screw 60 is such that threading the screw into the bore exerts a lateral force on the spinal rod R pushing it toward one end of the opening 32. More specifically, as the set screw 60 is threaded into the bore 65, it gradually urges or pushes the spinal rod R toward the interface washer 50 and the second member 35. As depicted in the figures, the set screw is top-tightening; meaning that it is readily accessed directly posterior to the connection assembly. This feature reduces the lateral profile of the connection assembly and makes final tightening of the assembly much easier for the surgeon.

In the use of the connection assembly 30, the bone fastener 40 is engaged to a specific vertebra at a desired orientation. The rod R is manipulated so that the assembly 30, which has been pre-threaded on the rod is aligned with the stem 42 so the second member 35 can be dropped onto the fastener with the stem 42 projecting through the second opening 36. As the rod R is nestled into position along the spine, the second member 35 pivots relative to the first member 31 attached to the rod. As the rod is finally positioned, the second member 35 floats along the stem until the final height alignment is achieved.

As the set screw 60 is threaded into the bore 65, it pushes the rod into contact with the rod groove 52 of the interface washer 50. Continued tightening of the set screw urges the interface washer 50 against the stem 42 of the bone fastener 40. At this point, the connection assembly 30 has assumed its final height and angular orientation. With the first member 31 and second member 35 in their proper angular relationship, and with the connection assembly 30 at its proper height relative to the bone fastener 40, further tightening of the set screw pushes the stem 42 of the fastener into the contact end 37 of the elongated opening 36. Thus, the final clamping is effected between engagement tip 61 of the set screw 60, and the contact end 37 of the opening 36 of the second number 35. Further tightening of the set screw 60 to a predetermined torque value insures a firm connection between the rod R and the rod groove 52, and between the interface element 45 of the bone fastener 40 and element 54 of the interface washer 50. A torque limiting set screw 60 can be provided in which the head 62 of the screw shears off at a predetermined torque so that over-tightening of the set screw is avoided.

In a further aspect of the connection assembly 30, the interface washer 50 has a thickness T that is calibrated to permit solid tightening of the connection assembly 30 about the rod R and bone fastener 40. The interface washer 50 is disposed simultaneously over both the first member and the second member. Thus, the washer can maintain contact with the spinal rod R before it is urged to the end of the opening 32. In addition the washer can maintain contact with the stem 42 of the bone fastener 40 when the stem is pressed into the contact end 37 of the elongated opening 36.

Additional embodiments of the present invention are depicted FIGS. 11–18. One embodiment includes a spinal implant assembly that also permits similar variable angle and variable height adjustments to the position of the bone fastener relative to an elongated spinal implant. The spinal implant assembly includes a connection assembly 80, a bone fastener 84 and means for urging an elongated spinal implant represented as a rod R (see FIG. 11 and 13) against the bone fastener 84 and against a wall 83 of the connection assembly. The connection assembly 80 includes a one-piece body having a bone fastener opening 81 and a spinal implant opening 82. The axes through the two openings are preferably mutually perpendicular, while the openings are elongated in the same direction and partially overlapping. The bone fastener opening 81 defines a width that allows the bone fastener 84 to be oriented at a variable angle in relation to the spinal implant R. The bone fastener opening 81 also defines a wall 86 at an end opposite the spinal implant opening 82. The wall 86 has an engaging surface 83 defining a plurality of radiating splines 90 as depicted in FIG. 12.

It is contemplated that the engaging surface 83 can include a raised pattern or knurling. The radiating splines, raised pattern, or knurling pattern is designed for interlocking engagement with the stem of the bone fastener 84. The connection assembly further defines a bore 89 intersecting the spinal implant opening. The bore 89 is designed to receive a means for urging the elongated spinal implant R to press against the bone fastener 84 and simultaneously urging the bone fastener 84 to press against the engaging surface 83 of the wall 86.

In this present embodiment, the spinal implant R is threaded through the spinal implant opening 82 and secured directly against the stem of the bone fastener 84 which is threaded through the bone fastener opening. Similar to what has been described for previous embodiments, the means for urging can include a set screw 88 threaded through the bore 89. The set screw 88 has an engagement tip that is configured to contact the spinal implant R. As depicted in FIGS. 11 and 13, the set screw is top-tightening and thus is readily accessible. Since the interface washer is not required with this present embodiment, fewer parts make the implantation assembly easier for the surgeon. One configuration of the bone fastener 84 can include a cylindrical stem having a surface configured with elongated projecting ribs 87. The ribs can form interlocking engagement with the engaging surface 83 of the connection assembly 80.

A preferred configuration of the bone fastener to be used with the connection assembly 80 is depicted in FIG. 14. This bone fastener 91 includes an elongated stem 92 having four substantially flat sides. The surface of each substantially flat side defines at least one projecting ribs 94 to provide solid engagement between the bone fastener and the engaging surface 83 of the connection assembly 80.

It is contemplated that if the fastener has a bone engaging screw 93, an internal hex can also be configured at the distal end of the stem to engage a tool for driving the screw 93 into a bone. It is also contemplated that a fastener being a bolt or a bone hook can also be used with the connection assembly 80.

The first member 31 as described must be pre-loaded onto the rod. However, the member can be configured for top-loading onto the rod by incorporating the top-loading features of the connector depicted in FIG. 4 of U.S. Pat. No. 5,562,662 as described at column 7, lines 10–13, and as depicted in FIGS. 3A–3C and described at column 5, line 56–column 8, line 11, which descriptions are incorporated herein by reference.

In addition, in the illustrated embodiment the means for urging, or set screw 60, is engaged within the first member 31. Alternatively, the clamping force can be applied at the second member 35. In this instance, the tip of the set screw would preferably be modified from the configuration shown in FIG. 10 of the present application. This alternative arrangement for the means for urging can be configured like the connector shown in FIGS. 3A–3C of the '662 Patent and described at column 5, line 6–column 8, line 11, which description has been incorporated by reference. With this alternative approach, the set screw would act against the stem 42 of the bone fastener 40 to push the stem against the washer 50, which then urges the rod R against the opposite end of the opening 32.

The bone fastener 40 has been described as including a generally circular cross-section stem 42. Non-circular cross-sections can be utilized provided hat the shape accommodates solidly clamping the stem 42 within the opening 36 in the second member. The contact end 37 of the opening 36 can have a complementary shape. As a further alternative, either or both the contact end 37 and stem 42 can have a surface roughening or interdigitating feature to enhance the clamping effect and resistance against slipping. The washer 50 is described as including a groove 52 for clamping the rod R. Other clamping features are contemplated that provide a solid fixation to the rod. In addition, the clamping feature can be modified to accommodate variations in the shape of the elongated spinal implant. For instance, the rod R can have a non-circular cross section.

In one of the illustrated embodiments, the two members 31 and 35 are connected by a connecting means 39 that permits relative rotation between the two components. Alternatively, the connecting means can provide for variable lateral separation between the two members, either alone or with the relative rotation capability. Thus, where the connecting means 39 includes the threaded post 70 and bore 71, the thread pitch can be modified to permit coarse adjustments in the lateral separation as one member is rotated relative to the other.

In yet another alternative embodiment, the interface element 45 on the bone fastener 40 can have varying degrees of prominence. In the illustrated embodiment, the interface element or rib 45 projects 0.04–0.10 inches from the stem 41. The rib can project farther from the stem, with a commensurate decrease in the thickness T of the interface washer 50.

Figure 15:
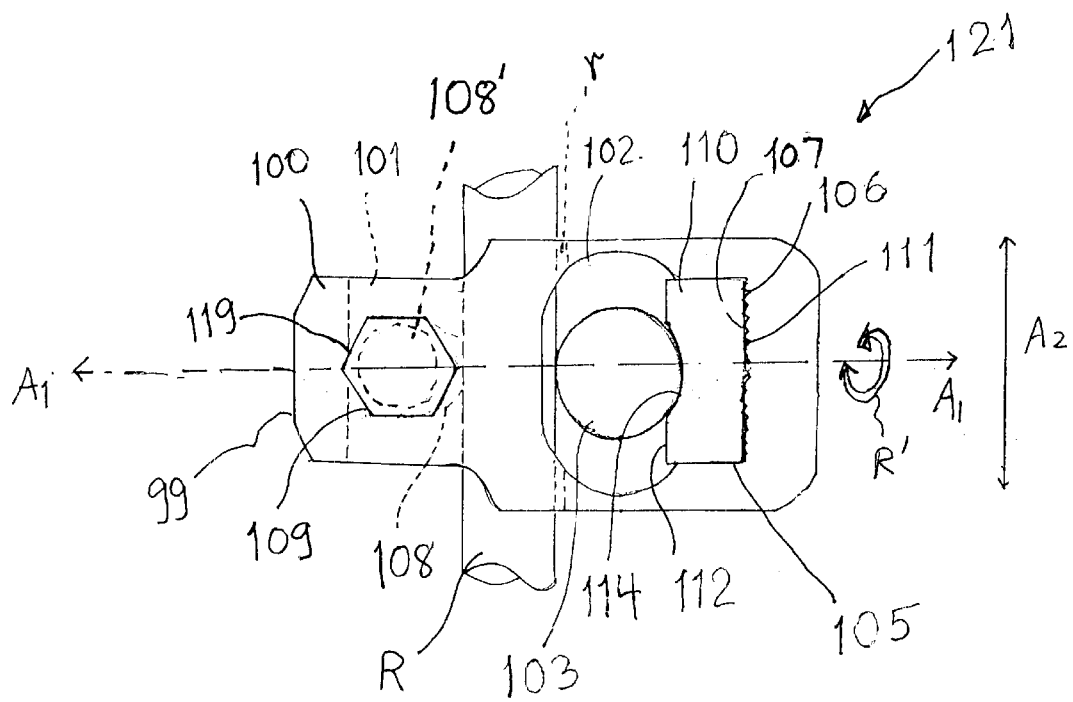
FIG. 15 is a top elevational view of a spinal implant assembly in accordance with a preferred embodiment.
Figure 16:
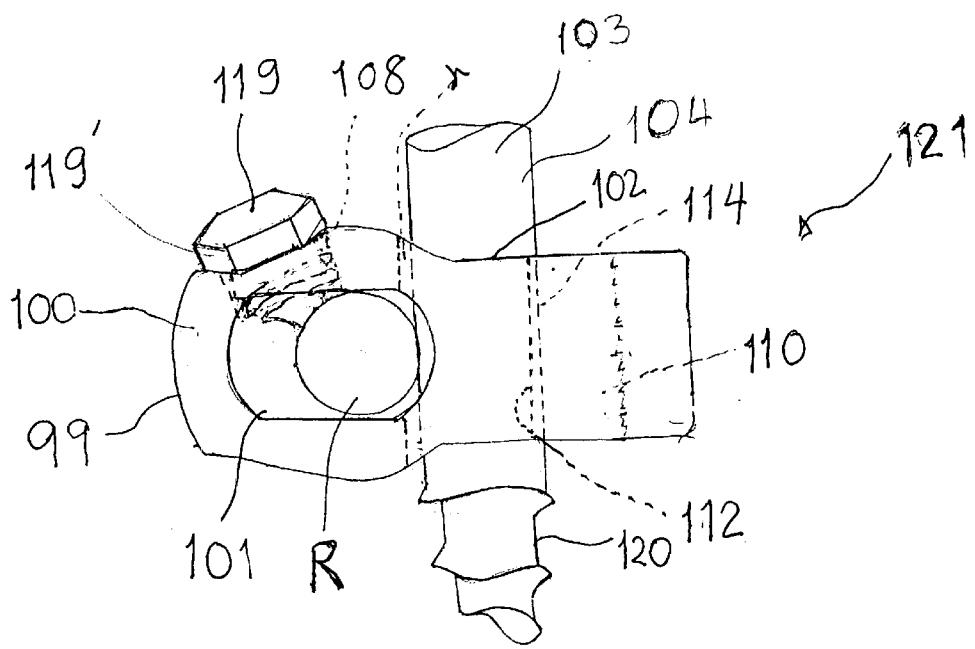
FIG. 16 is a side elevational view of the spinal implant assembly shown in FIG. 15.

In accordance with another embodiment of the present invention as shown in FIGS. 15–16, a connection assembly 99 includes a body 100. The body 100, as better seen in FIG. 17, defines a first opening 101 and a second opening 102. The first opening 101 is configured for receiving an elongated spinal implant or rod R therethrough, and the second opening 102 is configured for receiving a bone fastener 103. More particularly, the second opening 102 is sized to slidingly receive the elongated stem 104 of the bone fastener 103. The first opening 101 is elongated along a first axis A1 and second opening 102 is elongated along a second axis A2 substantially perpendicular to the first axis A1 as shown in FIG. 15. In addition, the first opening 101 is overlapping the second opening 102 in the region designated r. This overlapping region allows the spinal implant R to come in direct contact with the elongated stem 104 of the bone fastener 103 when the stem extends through the second opening 102.

As illustrated in FIG. 17, the second opening 102 defines a plug slot 105 for receiving a plug 110 as shown in FIGS. 15–16. The plug slot 105, which is disposed at an end of the second opening 102 opposite the overlapping region r, defines a wall 106 at the end opposite the first opening 101. The wall 106 defines an engagement surface 107 which preferably includes a plurality of radiating splines. It is contemplated that the engagement surface 107 may alternatively include a raised or a knurling pattern. The plurality of radiating splines, raised pattern, or knurling pattern is designed for interlocking engagement with the plug 110.

Turning now to FIGS. 18–19, the plug 110 is a circular disk sized to fit snugly into the plug slot 105. The plug 110 has a mating surface 111 configured to be matable to the engagement surface 107 of the wall 106 (see FIG. 17). The mating surface 111 shown in FIG. 19 defines a plurality of radiating splines 115 converging at the center 117 of the plug 110. Alternatively, the mating surface 111 can define other raised patterns, such as in the nature of cross hatching, multi-faceting, or knurling. Of course, it is to be understood that the pattern of the mating surface 111 of the plug 110 should complement the pattern of the engagement surface 107 of the wall 106 (see FIG. 17) in order for the plug to form an interlocking engagement with the wall and prevent rotational or translational shift in the final configuration of the connection assembly.

As illustrated in FIG. 18, the plug 110 defines a second surface 112 which faces the elongated stem 104 of the bone fastener 103, when the plug is in its operative position as depicted in FIGS. 15–16. The second surface 112 of the plug preferably defines a groove 114 for receiving the elongated stem 104 of the bone fastener 103. The groove most preferably is formed at a diameter slightly less than the diameter of the elongated stem 104 for an enhanced "3-point-shear clamp" feature of the TSRH® system. While the preferred embodiment of the present invention contemplates the use of the groove 114 for a circular elongated stem of the bone fastener, other clamping or attachment mechanisms are contemplated. For example, the elongated stem of the bone fastener can be formed of a relatively softer material than the plug 110, while the second surface 112 of the plug 110 can include surface features configured to penetrate the elongated stem or vice versa.

Similarly, while the preferred embodiment of the present invention envisions complementary engagement patterns between the mating surface of the plug and the engagement surface of the wall, other interlocking or attachment mechanisms can be implemented. For example, the mating surface 111 of the plug 110 can be formed of a relatively softer material than the engagement surface 107 of the wall 106, while the engagement surface 107 of the wall 106 may include surface features configured to penetrate the mating surface 111, or vice versa. Also contemplated are other surface interlocking arrangements that can solidly fix the plug 110 to the wall 106 to prevent relative movement under typical spinal loads.

Returning again to FIGS. 15–16, the body 100 further defines a first bore 108 including a bore opening 108'. The first bore 108 which intersects the first opening 101 at an end opposite the second opening 102 is configured to receive a means for urging 109. The urging means includes an urging member 119 extending through the first bore 108. The urging member can be a set screw 119'. Thus, the first bore 108 is threaded to receive the set screw 119'. The arrangement and alignment of the threaded first bore 108 and set screw 119' are such that threading the screw into the bore exerts a lateral force on the spinal implant R pushing it toward one end of the first opening 101. More specifically, as the set screw 119' is threaded into the bore 108, it gradually urges or pushes the spinal implant R to press against the elongated stem 104 of the bone fastener 103. Subsequently, the elongated stem 104 of the bone fastener 103 is pressed against the plug 110, which ultimately is pressed against the wall 106. As depicted in the figures, the set screw is top-tightening; meaning that it is readily accessed directly posterior to the connection assembly. This feature reduces the lateral profile of the connection assembly and makes final tightening of the assembly much easier for the surgeon.

In accordance with the present invention, as shown in FIGS.15–16, a spinal assembly 121 includes the connection assembly 99 described herein above and a bone fastener 103. The spinal assembly is provided to permit variable angle and variable height adjustments to the position of the bone fastener relative to an elongated spinal implant R. The elongated spinal implant R can take a variety of forms, such as a rod or a plate. As a rod, the spinal implant can have a circular or a non-circular cross-section that is preferably configured to permit attachment of the connection assembly 99 at various positions along the length of the implant. Preferably, although not essentially, the spinal implant can also be configured to permit rotation of the connection assembly about the longitudinal axis of the implant.

As shown in FIG. 16, the bone fastener 103 includes a bone engaging portion 120 that is configured for attachment to a portion of the spine. In the illustrated embodiment, the bone engaging portion 120 constitutes bone engaging threads in the nature of a pedicle screw. As indicated above, other bone attachment configurations are contemplated by the invention. The fastener 103 also includes an elongated stem 104 at the top portion of the fastener. Preferably, the elongated stem 104 is cylindrical, smooth and can rest snugly on the groove 114 of the plug 110. An internal hex (not shown) can be provided at the top end of the elongated stem 104 for engaging a tool for screwing the bone fastener 103 into a vertebra. Alternatively, an external hex or driving portion can be provided for engagement by an appropriate driving tool. Where the bone fastener 103 is a spinal hook, the internal hex is not essential, but gripping recesses may be added to the stem.

In the use of the spinal assembly 121 as illustrated in FIGS. 15–16, the bone fastener 121 is engaged to a specific vertebra at a desired orientation. The spinal implant R has been pre-threaded on the connection assembly 99 through the first opening 101 as it is nestled into position along the spine. The connection assembly 99 is aligned with the bone fastener 103 such that the elongated stem 104 is projecting through the second opening 102. The plug 110 is inserted into the plug slot and rotated about the first axis A1 in the direction of R' until the groove 114 properly receives the elongated stem 104 at a desired angular orientation and a desired height. As the set screw 119' is threaded into the bore 108, it pushes the spinal implant R into contact with the elongated stem 104 of the bone fastener 103. Continued tightening of the set screw urges the elongated stem 104 to press on the groove 114 on the plug 110 and consequently press the plug 110 against the wall 106. At this point, the spinal assembly 121 has assumed its final height and angular orientation. However, if necessary, both height and angular readjustment are possible and easy, especially in the case in which the bone fastener 103 is a bone hook. Since both the set screw 119' and the plug 110 are accessible from the top side of the connection assembly 99, it is easy for the surgeon to loosen the set screw 119', adjust the bone fastener 103 to a new position, rotate the plug 110 to properly receive the elongated stem 104 of the bone fastener 103 in its groove 114, and retighten the set screw 119'. This process can be accomplished without disturbing the rest of the spinal assembly system.

Figure 20:
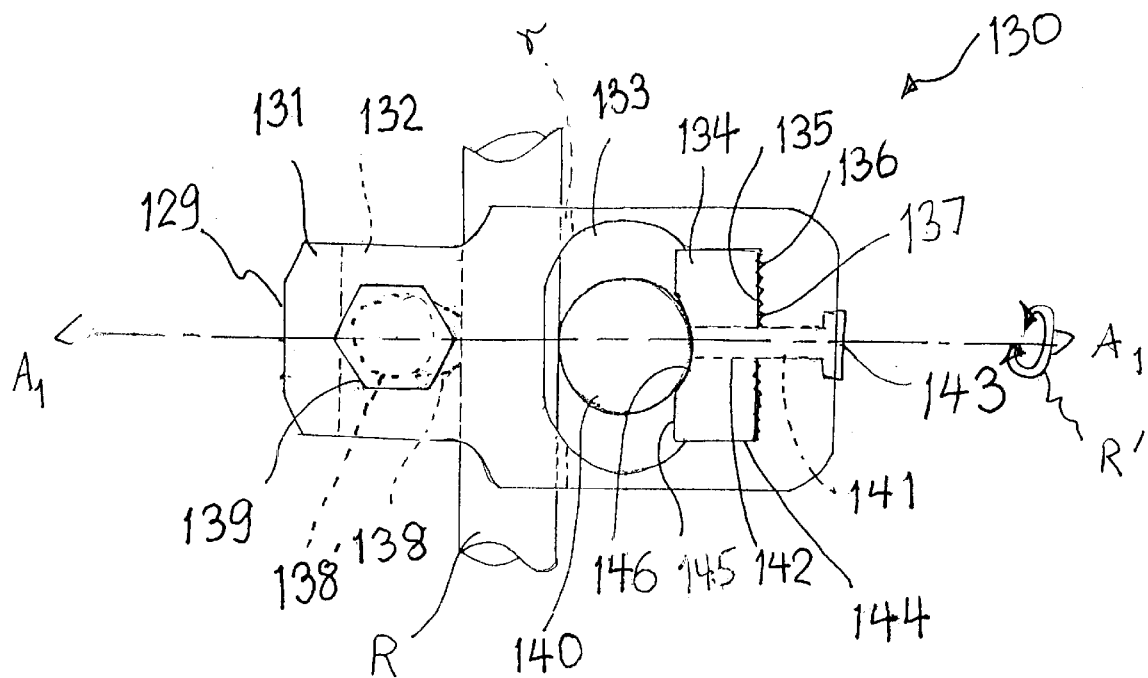
FIG. 20 is a top elevational view of a spinal implant assembly in accordance with another embodiment.
Figure 21:
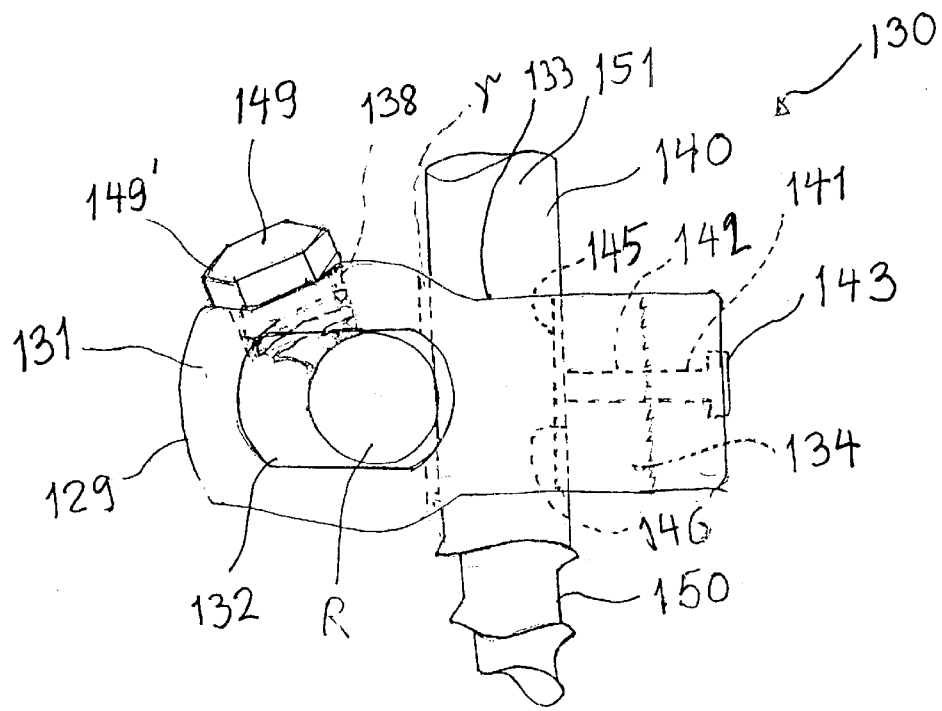
FIG. 21 is a side elevational view of a spinal plant assembly as shown in FIG. 20.

Turning now to FIGS. 20–21, in yet another embodiment of the present invention, a spinal assembly 130 includes a connection assembly 129 and a bone fastener 140. The spinal assembly 130 also is provided to permit variable angle and variable height adjustments to the position of the bone fastener relative to an elongated spinal implant R. The connection assembly 129 includes substantially the same features as the connection assembly 99 shown in FIGS. 15–16. The connection assembly 129 includes a body 131 which defines a first opening 132 and a second opening 133. The first opening 132 is configured for receiving an elongated spinal implant or rod R therethrough, and the second opening 133 is configured for receiving a bone fastener 140. More particularly, the second opening 133 is sized to slidingly receive the elongated stem of the bone fastener. The first opening 132 is elongated along a first axis A1 and second opening 133 is elongated along a second axis A2 substantially perpendicular to the first axis. The first opening 132 is overlapping the second opening 133 at a region designated r. The overlapping region r allows the spinal implant R to come in direct contact with the elongated stem 151 of the bone fastener 140 as depicted in FIGS. 20–21.

The second opening 133 includes a plug slot 144 for receiving a plug 134. The plug slot 144 which is disposed at an end opposite the first opening 132 defines a wall 135 opposite the first opening. The wall includes an engagement surface 136 which defines a plurality of radiating splines or a raised pattern as described previously. The body 131 further defines a first bore 138 intersecting the first opening 132 at an end opposite the second opening 133, and a second bore 141 intersecting the plug slot 144 at the center of the wall 135. The first bore 138 including a bore opening 138' is configured to receive a means for urging 139 which includes an urging member 149 extending through the first bore 138.

Figure 22:
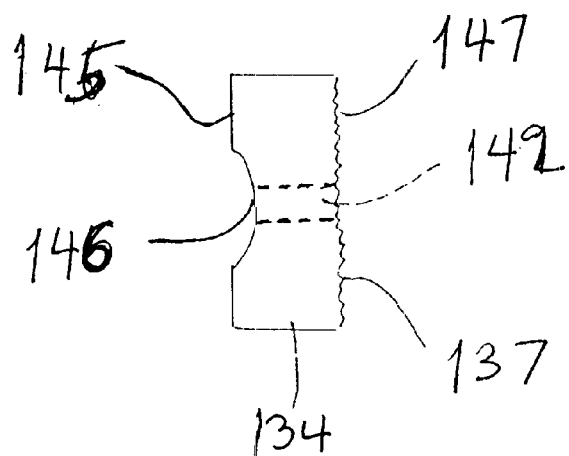
FIG. 22 is a top elevational view of a plug in accordance with the embodiment shown in FIGS. 20–21.
Figure 23:
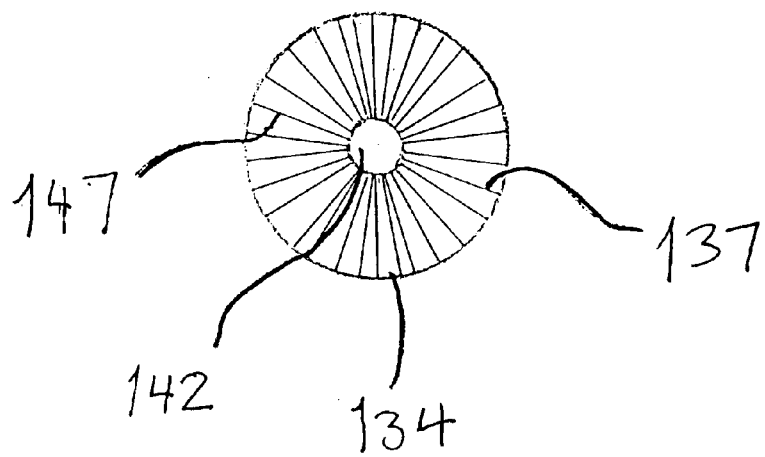
FIG. 23 is a side elevational view of the plug shown in FIG. 22.

Turning now to FIGS. 22–23, the plug 134 is a circular disk sized to fit into the plug slot 144 and is rotatable about the first axis A1 in the direction of R' (see FIGS. 20–21). In particular, the plug 134 defines a center bore 142 which, regardless of the rotational position of the plug 134 in the plug slot, is always in alignment with the second bore 141 of the body 131. The plug 134 defines a mating surface 137 which may include a plurality of radiating splines 147 or other surface design that is matable with the engagement surface 136 of the wall 135. Similar to what previously described, the plug 134 also defines a second surface 145 that includes a groove 146 for receiving the elongated stem 151 of the bone fastener 140 as illustrated in FIGS. 20–21.

In this particular embodiment, the connection assembly 129 further includes a securing means 143 for securing the plug 134 to the body 131. The securing means 143 includes a securing member 143' extending through the second bore 141 and the center bore 142. The securing member 143' can be a second set screw or a rivet. Where the securing member 143' is a second set screw, both the second bore 141 and the center bore 142 are threaded to properly receive the second set screw.

In the use of the spinal assembly 130 as illustrated in FIGS. 20–21, the spinal implant R has been pre-threaded on through the first opening 132 of the connection assembly 129. The bone fastener 140 which has been engaged to a specific vertebra is aligned with the connection assembly 129 such that the elongated stem 151 is projecting through the second opening 133 and the connection assembly 129 is positioned at a desired height. After the plug 134 has been inserted into the plug slot, it is rotated along the first axis A1 in the direction of R' until the groove 146 properly receives the elongated stem 151 at a desired angular orientation and a desired height. Then, the securing member 143' is threaded through the second bore 141 of the body 131 and the center bore 142 to tightly secure the plug 134 against the wall.

As the urging member 149, which can include a set screw 149', is threaded into the bore 138, it pushes the spinal implant R into contact with the elongated stem 151 of the bone fastener 140. Continued tightening of the set screw urges the elongated stem 151 to press on the groove 146 and consequently press the plug 134 against the wall 135. At this point, the mating surface 147 of the plug forms an interlocking engagement with the engagement surface 136 of the wall 135, and the spinal assembly 130 assumes its final height and angular orientation. However, if a readjustment is required, the plug 134 can be released from the engagement wall 135 by loosening both the urging member 149 and the securing member 143'. The repositioning of the bone fastener 140 can be made followed by the rotation of the plug 134 to properly receive the elongated stem 151 of the bone fastener 140. In this way, other components of the spinal implant system need not be disturbed. Alternatively, the bone fastener 140 and the plug 134 can be maintained at the original position while the body 131 of the connection assembly 129 is pivoted to assume a new position. Finally, the urging member 149 and the securing member 143' can be retightened.

Yet another alternative is to only loosely secure the plug 134 within the plug slot 144 with the securing member 143', while allowing the plug to freely rotate in the direction of R' about the first axis A1. The plug 134 is pressed in place against the wall 135 only after the application of the clamping force created from tightening the urging member 149. This alternative feature allows the readjustment of the spinal implant assembly to be performed easily only by loosening and tightening the urging member 149. More specifically, when the urging member 149 is loosened, the plug 134 can be adjusted rotationally to properly receive the elongated stem of the bone fastener. Afterward, the urging member can be tightened to solidly fixed all the components in a proper position.

Figure 24:
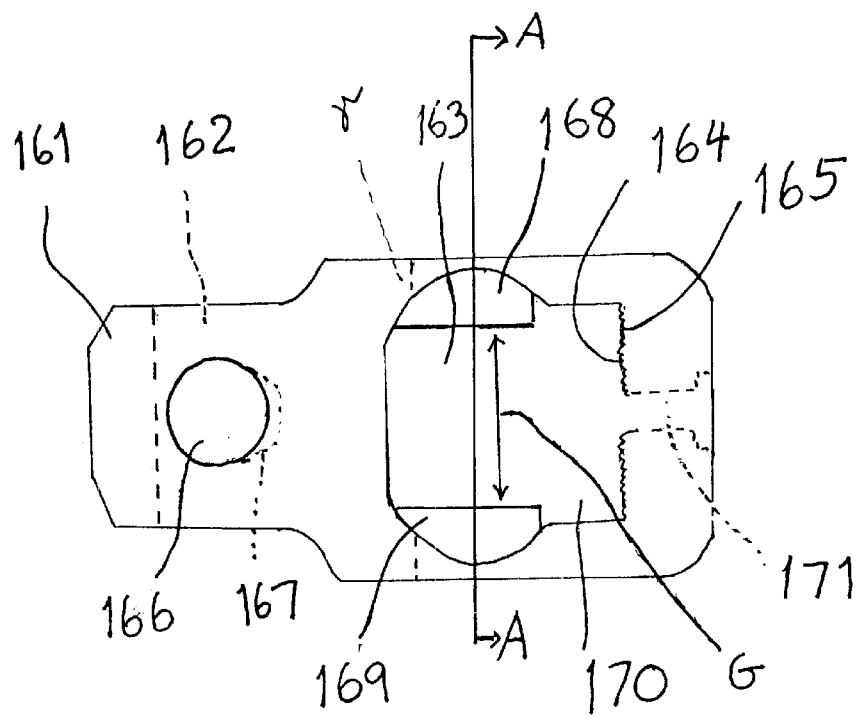
FIG. 24 is a top elevational view of a body of a connection assembly in accordance with yet another embodiment.
Figure 25:
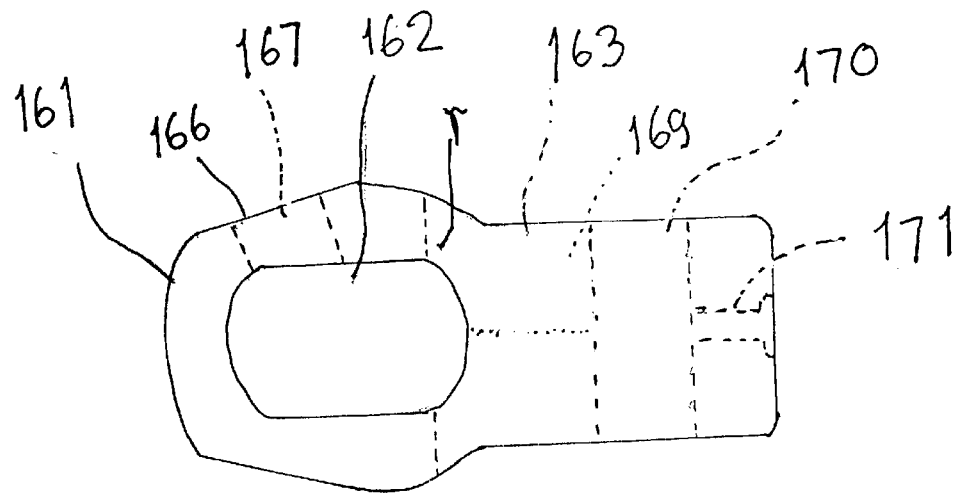
FIG. 25 is a side elevational view of the body of a connection assembly as shown in FIG. 24.
Figure 26:
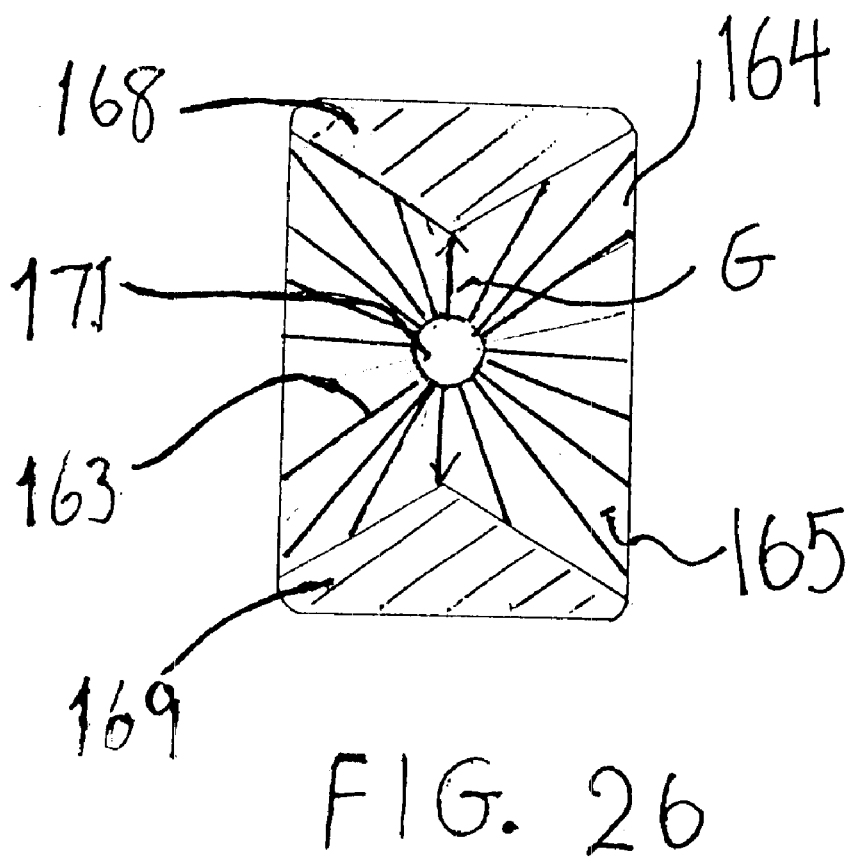
FIG. 26 is a cross-sectional view of the body of the connection assembly as viewed in the direction of the A—A arrows as shown in FIG. 24.

Turning now to FIGS. 24–26, in accordance with another embodiment, a connection assembly includes a body 161 which includes all the features described for the body 131 in the previous embodiment. The body 161 defines a first opening 162, an overlapping second opening 163 including a plug slot 170. Intersecting the first opening 162 is a first bore 167 having a bore opening 166 for receiving an urging member. The second opening defines a wall 165 which includes an engagement surface 164. The body 161 further defines a second bore 171 intersecting the plug slot 170. The additional features on this body 161 include a first side wall 168 and a second side wall 169 disposed within the second opening 163. The side walls are raised and converging toward one another leaving a gap G at the center of the second opening 163 sufficient for receiving the elongated stem of the bone fastener. Thus, in this embodiment, the gap G of the second opening 163 essentially acts as a fulcrum about which the body 161 can be pivoted relative to the elongated stem of the fastener to properly orient the body.

With this embodiment, the raised walls converge at a predetermined angle based upon the anticipated range of angular orientation of the bone fastener relative to the body 161 of the connection assembly. As illustrated in FIG. 26, the engagement surface 164 of the wall 165 includes a plurality of radiating splines converging toward the second bore 171. Of course, other surface patterns as described herein above are contemplated.

While in the illustrated embodiments, the bone fastener is a bone screw, it is understood that other bone fasteners are contemplated, such as various types of vertebral hooks and bone bolts. In addition, the principles of the invention can be applied to other spinal implant components that are not necessarily engaged to a vertebra. For instance, variable angle and variable length positioning can be contemplated in connection with a transverse connector between two spinal implants running generally parallel to each other along a length of the spine. Moreover, a laterally extending component can be attached to a spinal implant using the present inventive connection assembly, where other implants, such as bone fasteners, are attached to the laterally extending component.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

For example, the bone fastener 103 has been described as including a generally circular cross-section stem 104. Non-circular cross-sections can be utilized provided that the shape accommodates solidly clamping the elongated stem 104 within the groove 114 on the plug 110. The elongated stem 104 can also have projecting ribs or other surface features configured to penetrate the surface of the groove 114 of the plug 110 to enhance the clamping effect and resistance against slipping.

What is claimed is:

1. A connection assembly for connecting an elongated spinal implant, configured to span a length of the spine, to a bone fastener having an elongated stem at one end and an opposite end configured to engage a bone of the spine, the assembly comprising:
   a body defining;
      a first opening sized to receive the elongated spinal implant therethrough, said first opening being elongated along a first axis, and
      a second opening sized to allow variable angular placement of the bone fastener therethrough, said second opening being elongated along a second axis substantially perpendicular to said first axis, said second opening overlapping said first opening to allow direct contact between the elongated spinal implant and the elongated stem of the bone fastener therein, said second opening defining a plug slot opposite said first opening, said plug slot including a wall opposite said first opening and defining an engagement surface thereon;
   a plug insertable within said plug slot, said plug defining a mating surface interlockingly matable to said engagement surface of said wall, and a second surface defining a groove for contacting the elongated stem of the bone fastener; and
   means for urging the elongated spinal implant against the elongated stem of the bone fastener and simultaneously urging the elongated stem of the bone fastener against said plug and said plug against said engagement surface of said wall.

2. The connection assembly according to claim 1 wherein said engagement surface of said wall includes a raised pattern and said mating surface of said plug includes a complementary raised pattern.

3. The connection assembly according to claim 2 wherein said engagement surface of said wall includes a plurality of radiating splines and said mating surface of said plug includes a plurality of complementary radiating splines.

4. The connection assembly according to claim 1 wherein said body includes a first side wall and a second side wall, said side walls converging toward the center of said second opening leaving a gap sufficient to receive the bone fastener therethrough.

5. The connection assembly according to claim 1 wherein said body further defines a first bore intersecting said first opening at an opposite end of said wall for receiving said urging means.

6. The connection assembly according to claim 5 wherein said means for urging includes an urging member extendable through said first bore to contact a spinal implant.

7. The connection assembly according to claim 6 wherein said urging member is a set screw, and said first bore is threaded to receive said set screw.

8. The connection assembly according to claim 1 further comprises a bone fastener having an elongated stem at one end and an opposite end configured to engage a bone of the spine.

9. The connection assembly according to claim 8 wherein said elongated stem of said bone fastener is cylindrical and sized to fit said groove on said second surface of said plug.

10. A connection assembly for connecting an elongated spinal implant, configured to span a length of the spine, to a bone fastener having an elongated stem at one end and an opposite end configured to engage a bone of the spine, the assembly comprising:
    a body defining;
       a first opening sized to receive the elongated spinal implant therethrough, said first opening being elongated along a first axis, and
       a second opening sized to allow variable angular placement of the bone fastener therethrough, said second opening being elongated along a second axis substantially perpendicular to said first axis, said second opening overlapping said first opening to allow direct contact between the elongated spinal implant and the elongated stem of the bone fastener therein, said second opening defining a plug slot opposite said first opening, said plug slot including a wall opposite said first opening and defining an engagement surface thereon;
    a plug insertable within said plug slot, said plug having a mating surface interlockingly matable to said engagement surface of said wall, and a second surface defining a groove for contacting the elongated stem of the bone fastener, said plug defining a center bore alignable with a second bore of said body when said plug is within said plug slot;
    means for urging the elongated spinal implant against the elongated stem of the bone fastener and simultaneously urging the elongated stem of the bone fastener against said plug and said plug against said engagement surface of said wall; and
    securing means extending through said center bore and said second bore for securing said plug to said body.

11. The connection assembly according to claim 10 wherein said engagement surface of said wall includes a raised pattern and said mating surface of said plug includes a complementary raised pattern.

12. The connection assembly according to claim 11 wherein said engagement surface of said wall includes a plurality of radiating splines and said mating surface of said plug includes a plurality of complementary radiating splines.

13. The connection assembly according to claim 10 wherein said body includes a first side wall and a second side wall, said side walls converging toward the center of said second opening leaving a gap sufficient to receive the bone fastener therethrough.

14. The connection assembly according to claim 10 wherein said body further defines a first bore intersecting said first opening at an opposite end of said wall for receiving said urging means.

15. The connection assembly according to claim 14 wherein said means for urging includes an urging member extendable through said first bore to contact a spinal implant.

16. The connection assembly according to claim 15 wherein said urging member is a set screw, and said first bore is threaded to receive said set screw.

17. The connection assembly according to claim 10 further comprises a bone fastener having an elongated stem at one end and an opposite end configured to engage a bone of the spine.

18. The connection assembly according to claim 17 wherein said elongated stem of said bone fastener is cylindrical and sized to fit said groove on said second surface of said plug.

19. The connection assembly according to claim 10 wherein said securing means includes a securing member extendable through said center bore and said second bore.

20. The connection assembly according to claim 19 wherein said securing member is a second set screw, and said center bore and said second bore are threaded to receive said second set screw.

* * * * *